US006576195B1

(12) United States Patent
Eppes

(10) Patent No.: US 6,576,195 B1
(45) Date of Patent: Jun. 10, 2003

(54) TIME-LAPSED IC DEFECT ANALYSIS USING LIQUID CRYSTAL

(75) Inventor: David Harry Eppes, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/521,260

(22) Filed: Mar. 8, 2000

(51) Int. Cl.⁷ .............................................. G01N 21/47
(52) U.S. Cl. .................................................. 422/82.05
(58) Field of Search ........................... 438/14; 349/45; 437/209; 422/82.05

(56) References Cited

U.S. PATENT DOCUMENTS 6,284,197 B1 * 9/2001 Abbott .................... 422/82.05

OTHER PUBLICATIONS

D. L. Burgess and O. D. Trapp, *Failure and Yield Analysis Handbook*, Oct. 1992, pp. 7.9–7.16.
D. Burgess, *Electronic Failure Analysis: Seminar Reference, Liquid Crystal Hot Spot Detection*, ASM International, 1998, pp. 143–145.
*Failure Analysis of Integrated Circuits: Tools and Techniques*, Lawrence C. Wagner, Ed., 1999, pp. 70–77.
Khandekar, S and Wills, K. S., *Micro Electronic Failure Analysis: Liquid Crystal Microscopy*, ASM International, 1993, pp. 141–144.

* cited by examiner

*Primary Examiner*—John F. Niebling
*Assistant Examiner*—Andre'C Stevenson

(57) ABSTRACT

Defect analysis of an integrated circuit die is enhanced using a method and system that make possible the detection of defect-related heat generation in the die. According to an example embodiment of the present invention, a semiconductor die having a liquid crystal layer is analyzed by detecting a liquid crystal phase change caused by heating the die. The heating causes a first circuit region and a second circuit region to effect a separate phase change in corresponding areas of the liquid crystal layer. A detector is adapted to use time-lapsed analysis to detect the liquid crystal phase change in the area corresponding to the second circuit region before the corresponding areas cease to be separately detectable.

23 Claims, 5 Drawing Sheets

TIME-LAPSED IC DEFECT ANALYSIS USING LIQUID CRYSTAL

FIELD OF THE INVENTION

The present invention relates generally to semiconductor devices and their fabrication and, more particularly, to semiconductor devices and their manufacture involving techniques for analyzing and debugging circuitry within an integrated circuit.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of such high-density and high functionality in semiconductor devices has been the demand for increased numbers of external electrical connections to be present on the exterior of the die and on the exterior of the semiconductor packages which receive the die, for connecting the packaged device to external systems, such as a printed circuit board.

As the manufacturing processes for semiconductor devices and integrated circuits (IC) increase in difficulty, methods for testing and debugging these devices become increasingly important. Not only is it important to ensure that individual chips are functional, it is also important to ensure that batches of chips perform consistently. In addition, the ability to detect a defective manufacturing process early is helpful for reducing the number of defective devices manufactured.

One IC analysis method involves using a liquid crystal material. Liquid crystalline materials have both crystalline solid and liquid characteristics. These characteristics enable their use for thermally analyzing an integrated circuit for defects. When the liquid crystal material is heated, its properties change. These changes include, for example, a coloring change and an ordering transition. Available defect analysis methods use the changes as indications of temperature in an integrated circuit. Detecting the temperature and temperature variation of an IC is useful for detecting circuit defects that result in excessive current drain and, therefore generate excessive heat. By forming a liquid crystal layer on an integrated circuit, the response of the liquid crystal can be monitored and used to detect such "hot spots" that are an indication of a defect.

One type of liquid crystalline material useful for defect analysis is calamatic liquid crystal material having nematic ordering. Calamatic liquid crystals have long, rod-shaped molecules, and those having nematic ordering change under temperature variation from a nematic to an isotropic state. In the nematic state, the liquid crystal alters the polarization of light incident upon it. When the liquid crystal changes to an isotropic state, the polarization of incident light is no longer affected. This change in the effect upon incident light is used to detect a temperature change in the liquid crystal material. The transition temperature at which the change occurs is dependent upon the particular characteristics of the material.

Typical analysis methods that use liquid crystals involve forming a liquid crystal layer on an integrated circuit, heating the circuit with an external source, and observing a change in the state of the liquid crystal. The liquid crystal layer is often formed by adding a solvent, such as pentane, to the liquid crystal material and then applying the material to the surface of an integrated circuit device with an eye-dropper. The solvent evaporates, leaving the liquid crystal material behind. Other liquid crystal application methods include applying liquid crystal with a spreading strip, or applying a drop of liquid crystal on the chip and spinning the chip to spread out the liquid crystal. In addition, a liquid crystal emulsion may be used in place of the liquid crystal mixed with a solvent.

Once the liquid crystal has been applied, the integrated circuit is then heated with an external heater. The heater is used to bring the integrated circuit to within about 0.1 Kelvin of the transition temperature of the liquid crystal material. A microscope is directed at the liquid crystal layer. A suitable microscope includes a polarized light source and a linear polarizer (analyzer) in front of an eyepiece or camera. The integrated circuit is electrically stimulated, thereby heating a defect in the circuit and raising the liquid crystal material over the defect to its transition temperature. The liquid crystal material changes from nematic to isotropic phase, which is evidenced by a dark spot that is detected by the microscope.

One problem with currently used methods for liquid crystal IC analysis is associated with the detection of a defect-generated liquid crystal phase change when other heat sources, such as other defects or intrinsic heat sources, interfere with the defect-driven phase change. For example, intrinsic heat sources, such as phase lock loops (PLL) and crystal oscillators, generate heat during normal operation that tends to overwhelm defect-related heat sources in certain types of ICs. These intrinsic heat sources make liquid crystal analysis of defective ICs difficult because the intrinsic heat causes the liquid crystal to change phase at such a rate that liquid crystal phase changes due to defects are difficult or impossible to detect using conventional methods. These intrinsic heat sources make liquid crystal defect analysis particularly difficult when they are located in close proximity to the defect being sought.

SUMMARY OF THE INVENTION

The present invention is directed to a method and system for analyzing an IC die involving defect detection using liquid crystal. The defect detection can used to detect defects in dies having intrinsic heat sources that make conventional liquid crystal analysis difficult or even impossible. The present invention is exemplified in a number of implementations and applications, some of which are summarized below.

According to an example embodiment of the present invention, a semiconductor die having a liquid crystal layer is analyzed using time-lapsed analysis to detect a phase change of the liquid crystal caused by heat generated in the die. The heat causes a first circuit region and a second circuit region to generate heat and effect separate phase changes in corresponding areas of the liquid crystal layer. The first and second circuit regions are located in such a manner that the separate phase changes are not separately viewable using real-time analysis. A detection device, such as a videocamera, is adapted to use time-lapsed analysis to separately detect the phase changes of the liquid crystal and provide detection data for analysis of a defect in the die.

The above summary of the present invention is not intended to describe each illustrated embodiment or every implementation of the present invention. The figures and

BRIEF DESCRIPTION OF THE DRAWINGS

The invention may be more completely understood in consideration of the following detailed description of various embodiments of the invention in connection with the accompanying drawings, in which.

Figure 1A:
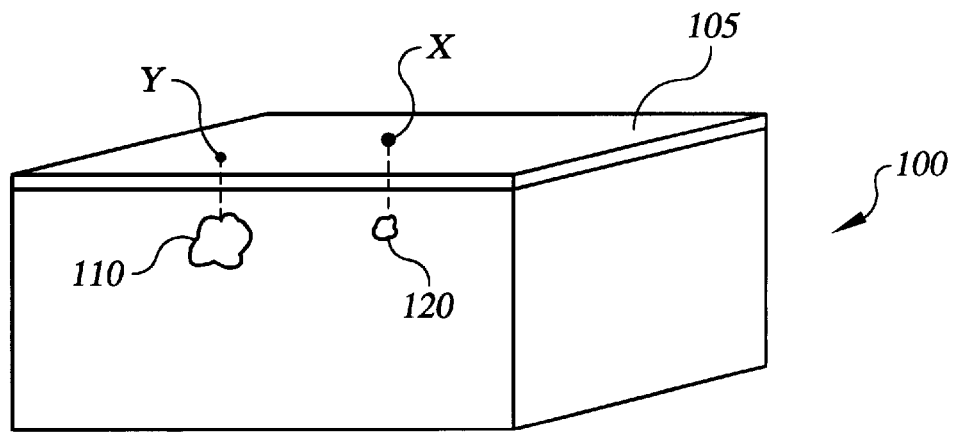
FIG. 1A is a semiconductor die having a liquid crystal layer, for use in accordance with an example embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable for a variety of different types of semiconductor devices, and the invention has been found to be particularly suited for IC dies requiring or benefiting from defect analysis involving the detection of a liquid crystal phase change due to heat in the die. While the present invention is not necessarily limited to such devices, various aspects of the invention may be appreciated through a discussion of various examples using this context.

In connection with an example embodiment of the present invention, it has been discovered that particular IC dies have internal heat sources that combine with defect heat sources to produce a combined heat that makes the separate detection of defect-generated heat difficult or impossible to achieve. In this example embodiment, liquid crystal is formed on the die, and the die is heated. As the die heats, the liquid crystal also heats and begins to change phase as it reaches its transition temperature. The phase change is due to the combined heat from the defect and other sources. The portion of the liquid crystal nearest the defect heats faster than the surrounding area and changes phase briefly before the surrounding liquid crystal does. This defect-generated phase change, however, is not detectable using real-time analysis, such as the human eye viewing the liquid crystal with a microscope. A time-lapsed analysis device, such as a videocamera, is arranged over the liquid crystal and adapted to detect the phase change related to the defect-generated heat before it is overwhelmed by heat generated elsewhere in the die.

Another problem sometimes encountered is associated with using intrinsic heat sources to generate heat in the die for liquid crystal analysis is due to the excessive amount of heat generated by particular intrinsic heat sources. In some instances, an intrinsic heat source can generate so much heat that liquid crystal analysis of defects using conventional detection methods is inhibited or even prevented. This is so because the heat generated at the intrinsic source can overwhelm the heat generated by defects, making a defect-generated liquid crystal phase change not detectable. However, in connection with another example embodiment of the present invention, it has been discovered that, when an image of the liquid crystal phase change is recorded and reviewed in slow motion, the liquid crystal phase change due to the defect can be detected. For additional information regarding the use of internal heat sources, reference may b made to U.S. patent application Ser. No. 09/521,627 entitled "Defect Detection Using Liquid Crystal and Internal Heat Source", filed concurrently herewith.

According to another example embodiment of the present invention, a semiconductor die having a liquid crystal layer is analyzed. A first circuit region is electrically operated, and the electrical operation causes the first circuit region and a second circuit region to effect a separately viewable phase change in corresponding areas of the liquid crystal layer. The first and second circuit regions are selected such that the corresponding phase changes cease to be separately viewable by conventional methods, such as by viewing the real-time phase change through a microscope. A detector is adapted to use time-lapsed analysis to detect the liquid crystal phase change in the area corresponding to the second circuit region before the corresponding areas cease to be separately viewable. In this manner, defects can be located in die circuitry that has significant intrinsic heat sources that overwhelm defect related heat sources.

Figure 1B:
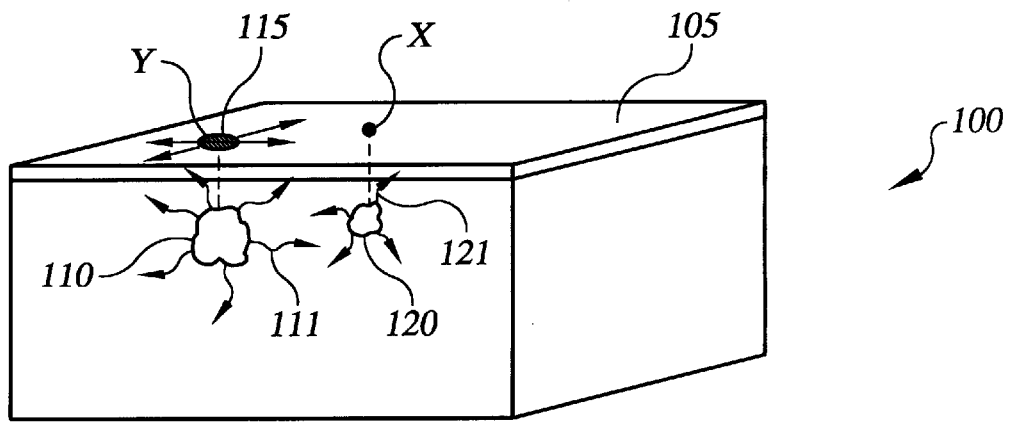
FIG. 1B is the semiconductor die of FIG 1A undergoing analysis, according to an example embodiment of the present invention.

For example, FIGS. 1A and 1B show a semiconductor die 100 undergoing liquid crystal analysis, according to an example embodiment of the present invention. The die has a first circuit region 110 and a second circuit region 120. A layer of liquid crystal material 105 having a transition temperature is formed over the die. Portions Y and X of the liquid crystal layer are located over the first and second circuit regions 110 and 120, respectively. Heat is generated in the die at FIG. 2, such as by electrically operating the die. The heat 111 generated at circuit region 110 is greater than and tends to overwhelm the effect of the heat 121 generated at circuit region 120. As the heat spreads from the circuit regions, the temperature of the surrounding portions of the die increases. The liquid crystal layer is also heated, and when it reaches its transition temperature, it undergoes a phase change viewable as a dark spot.

As the circuit region 110 generates heat, portion Y of the liquid crystal reaches its transition temperature and undergoes a phase change. The liquid crystal phase change beginning at portion Y expands radially, and the radial expansion has a leading edge 115. The heat from both of the circuit regions also reaches liquid crystal portion X. Since portion X is being heated by both circuit regions, it changes phase momentarily before the leading edge 115 of the expanding liquid crystal phase change reaches it. The selected circuit regions are so close that the phase change at portion X occurs at such a short time before being engulfed by the leading edge 115 that it ceases to be separately viewable by conventional means, such as by viewing the real-time phase change through a microscope. A detector is adapted to view the phase change at portion X before it ceases to become separately viewable, enabling liquid crystal analysis of the die 100 using an internal intrinsic heat source.

The liquid crystal layer may be formed using methods such as those described in the background hereinabove. According to another example embodiment of the present invention, a liquid crystal emulsion, such as BDH K15 liquid crystal, is placed on the die and formed into a substantially even layer over the die using a blast of air. The air blast is selected such that the volume and flow rate of air make possible the even formation of a liquid crystal layer over the die. By using such an application, the liquid crystal analysis described herein is enhanced.

According to a more particular example embodiment of the present invention, a semiconductor die having an intrinsic heat source and a liquid crystal layer is analyzed. A microscope having a polarized light source, an analyzer, and a camera is arranged over the die. An electrical power source is used to power the die, and the intrinsic heat source generates heat in response. For example, the power source may be operated in a continuous loop that includes operational conditions that induce a circuit failure in the die. The generated heat expands radially and heats other portions of the die including the liquid crystal. As the liquid crystal reaches its transition temperature, it changes phase. The phase change is detectable as a dark area when viewed with the microscope. The phase change of the liquid crystal begins near the intrinsic heat source and expands radially. In connection with this example embodiment, it has been discovered that, as the leading edge of the phase change expansion approaches a defect, the defect heats the portion of the liquid crystal over the defect and causes it to change phase shortly before being engulfed by the leading edge of the phase change resulting from the intrinsic source. This defect-driven phase change is recorded using the microscope and the camera and used to determine the location of the defect.

The type of liquid crystal used can be selected based upon the type of analysis that is to be performed. For example types of liquid crystal material suitable for use in connection with the present invention, reference may be made to T. W. Lee & S. V. Pabbisetty, *Liquid Crystal Microscopy*, in MICROELECTRONIC FAILURE ANALYSIS 141 ($3^{rd}$ ed., ASM International, 1993). Such liquid crystal is available from various sources and can be chosen to provide a state transition temperature (STT) that is just over room temperature for near-room temperature applications. Other liquid crystal material may be used in applications requiring or benefiting from different properties, such as liquid crystal having a STT that is higher or lower for applications where the testing is done at a different temperature.

According to another example embodiment of the present invention, the power supplied to the internal heat source is varied. For example, the power variation may include altering the frequency of the clock cycle being applied to the die. Higher frequencies operate the die at a faster rate and draw more power. Using a constant voltage source, the resulting current draw increases. Advantages of altering the power include enabling the control of the amount of heat generated by the internal heat source. This is useful for controlling the progression of the liquid crystal phase change. For faster advancement of the leading edge of the phase change, the clock frequency is manipulated to cause the intrinsic heat source to generate more heat. For slower advancement of the leading edge, the clock frequency is manipulated to cause the intrinsic heat source to generate less heat. The rate of heat generation can be controlled by increasing or decreasing the frequency of the clock. The power adjustments may, for example, be performed during the analysis process, or may be preset and held constant throughout the analysis process.

In another example embodiment of the present invention, spatial adjustments are made to keep the leading edge of the transition area within the field of view of the microscope. For example, it may be useful to move either the microscope or the die in order to maintain a desired view, particularly when the microscope is focused on a small area of the die. One example manner in which to maintain view of the leading edge of the liquid crystal transition is to mount the die on a moving platform, such as a microscope stage, and move the platform accordingly. Another manner is to move and re-focus the microscope itself on the leading edge of the transition. Still another method is to move both the die and the microscope.

In another example embodiment of the present invention, a cooling arrangement is used to cool the die as it is being analyzed in order to control the intrinsic heating process. For example, the intrinsic heat source may heat the die at such a rate that it is difficult or impossible to sufficiently analyze the die. By cooling the die, the heating rate, and thus the advancement of the leading edge of the transition area, can be slowed or even reversed. Slowing the heating rate helps for defect detection because more time is allowed for obtaining an image of the defect-generated liquid crystal transition before it is engulfed by the leading edge. Reversing the heating rate enables the reversal of the phase transition, allowing the viewing of the defect-generated transition as it transitions back into the original state. One example cooling arrangement includes a filtered compressed gas supply, such as an air supply or a nitrogen supply, adapted to direct the gas at the die.

The cooling arrangement may also be used to speed the analysis process. For example, once the general location of the defect is known, it may be advantageous to allow the die to heat at a fast rate until the leading edge nears the defect. When the defect is neared, the coolant can be used to slow the heat rate and thus slow the expansion of the leading edge as it approaches the defect. Depending upon the die being analyzed, the cooling arrangement can be adjusted to achieve a desired heating rate.

Another manner in which to make the detection of the defect easier is to use the camera to record an image of the liquid crystal phase change as a function of time. The recorded image can, for example, be viewed in slow motion, or viewed in a frame-by-frame mode. Each image (frame) captured by the camera is taken at a sufficiently short time interval that enables the capture of an image of the defect-driven phase change before the leading edge of the intrinsic heat source-driven phase change engulfs the defect. That is, the camera speed must be selected so that each frame is recorded at a time interval that is shorter than the time interval between the occurrence of the defect-driven phase change and the engulfing of the defect-driven phase change by the intrinsic heat-driven phase change. In one specific example embodiment, a real-time video camera, such as a Panasonic KR-212, is used to capture and record these images.

Figure 2A:
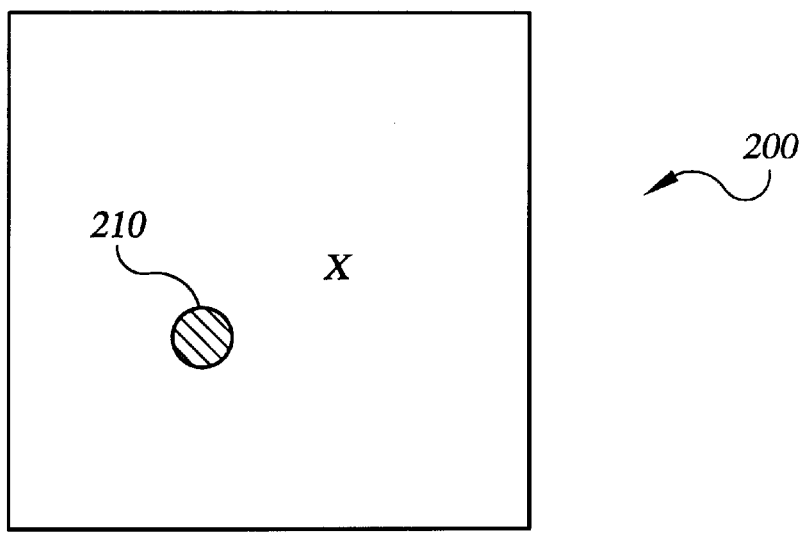
FIG. 2A is a top view of a semiconductor die undergoing analysis, according to another example embodiment of the present invention.
Figure 2B:
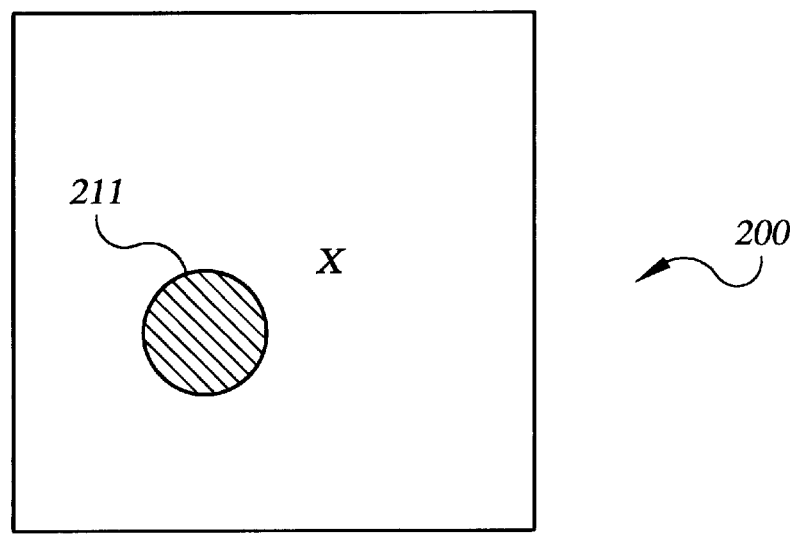
FIG. 2B is a top view of the semiconductor die of FIG. 2A, according to another example embodiment of the present invention.

FIGS. 2A–2D show camera images of a top view of a liquid crystal layer on a semiconductor die 200 changing phase as a result of heat generated in the die, according to another example embodiment of the present invention. The die 200 includes a defect below the liquid crystal layer, shown as X, and an intrinsic heat source. It should be noted that, although the camera images in FIGS. 2A–2D are shown in connection with heat generated with the intrinsic heat source, alternate heat sources including external heat sources may be used in place of or in connection with the intrinsic heat source to effect similar results. A camera is located over the die and is adapted to capture the images shown. The die is electrically stimulated and the intrinsic heat source generates heat that causes a portion 210 of the liquid crystal layer to change phase, as shown in FIG. 2A. As electrical stimulation continues to be applied to the die 200, the portion of the liquid crystal layer that has changed phase expands, shown as portion 211 in FIG. 2B.

Figure 2C:
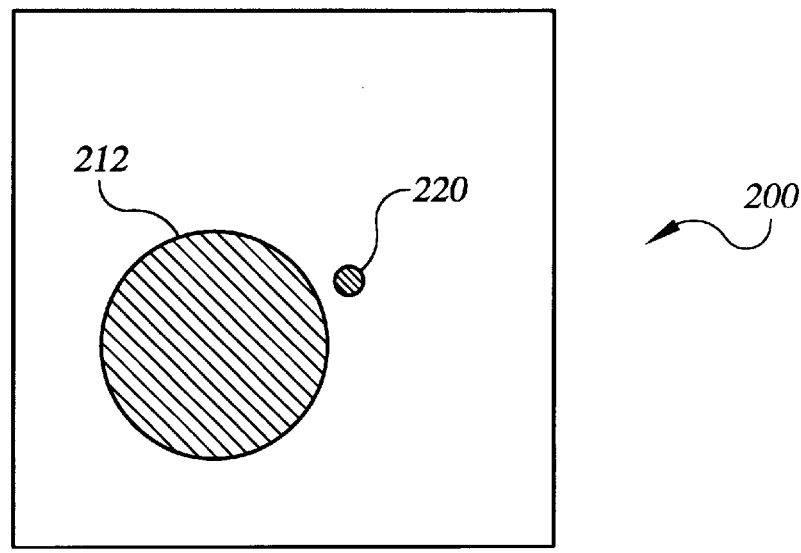
FIG. 2C is a top view of the semiconductor die of FIG. 2A, according to another example embodiment of the present invention.
Figure 2D:
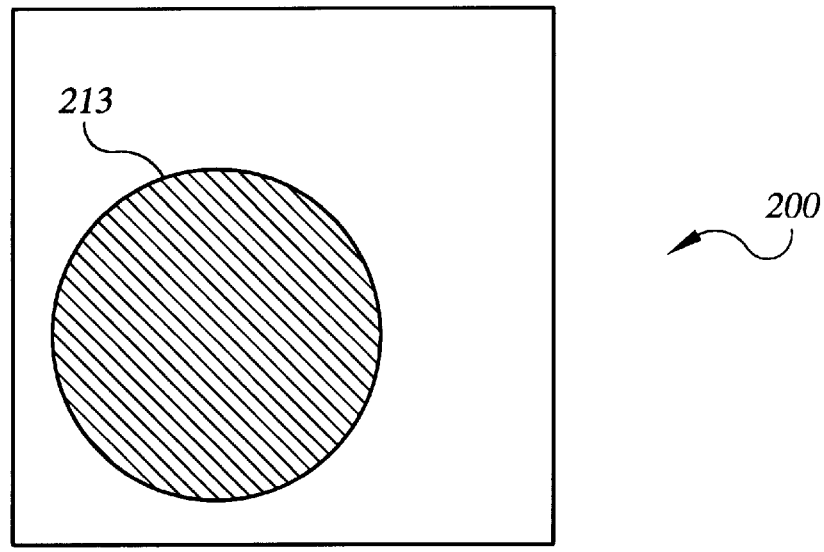
FIG. 2D is a top view of the semiconductor die of FIG. 2A, according to another example embodiment of the present invention.

In addition to the heat generated by the intrinsic heat source, the defect also generates heat. In FIG. 2C, the expanding area of liquid crystal having undergone a phase change 212 has nearly reached the portion of liquid crystal over the defect. At this point, the combined heat generated by the intrinsic heat source and the defect is sufficient to cause a portion 220 of the liquid crystal to change phase. The camera is adapted to capture the image of this phase change before the expanding area engulfs the portion 220, as shown in FIG. 2D.

Referring again to FIGS. 2C and 2D, and according to another example embodiment of the present invention, a cooling arrangement is used to reverse the phase transition, such as described herein above. If the transition to FIG. 2D occurs too fast, the application of a cooling arrangement can be used to reverse the transition so that the phase transition regresses to the image shown in FIG. 2C. In this manner, the defect can be detected even if the advancement of the phase transition is too rapid for analysis without a cooling arrangement. In addition, the power supply to the die can also be adjusted to control the amount of heat generated in the die and to enable the regression of the liquid crystal phase change from FIG. 2D to FIG. 2C. The power adjustment can be used alone or in conjunction with the cooling arrangement to achieve the desired result.

Figure 3:
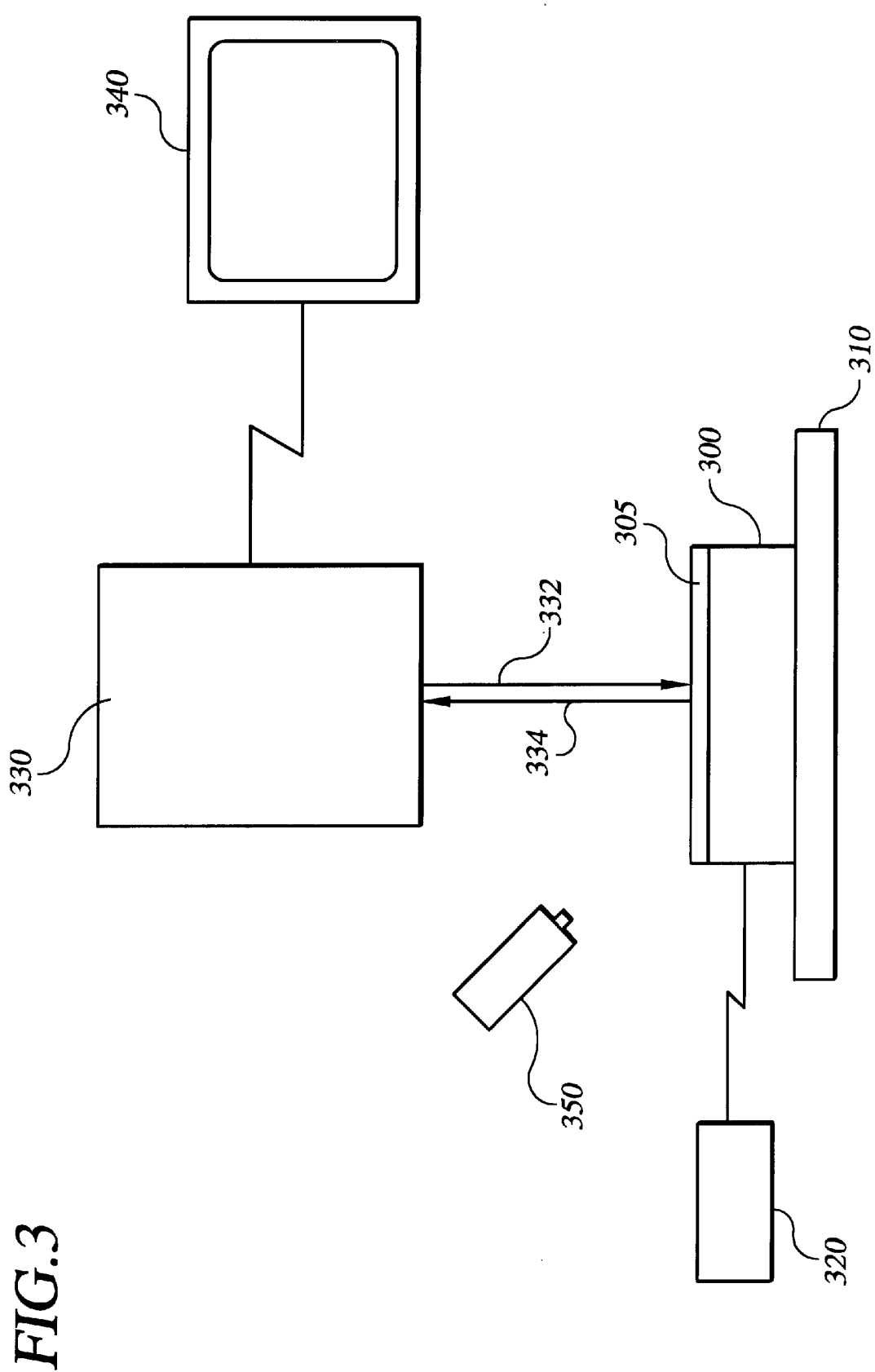
FIG. 3 is a system for analyzing a semiconductor die, according to another example embodiment of the present invention.

FIG. 3 is a system adapted to detect a defect using a liquid crystal phase change, according to another example embodiment of the present invention. The system may, for example, be used to create the images shown in FIGS. 2A–2D. The system includes a mounting platform 310 adapted to hold a semiconductor die 300 having a liquid crystal layer 305 and an intrinsic heat source. A power supply 320 is coupled and adapted to supply power to the die and to generate heat in the die via the intrinsic heat source. A detection arrangement 330 is arranged over the liquid crystal layer 305 and is adapted to capture an image of the liquid crystal as it changes phase due to heat generated by a defect and by the intrinsic heat source. A polarized light source is adapted to direct polarized light 332 at the die 300. An analyzer (linear polarizer) is arranged so that an image 334 from the die 300 passes through it before it is captured. The defect-related phase change occurs momentarily before a phase change generated by the intrinsic heat source in the die, such as discussed hereinabove. The detection arrangement 330 is adapted to capture the image before the defect-related phase change ceases to be separately viewable from the phase change caused by the intrinsic heat source. In an alternate example embodiment (not shown), an external heat source is arranged to supply additional heat to the die.

The detection arrangement optionally includes a monitoring arrangement 340 adapted to display an image of the phase change of the liquid crystal layer 305. In one implementation, the monitoring arrangement includes a video recorder adapted to receive the image data captured by the detection arrangement 330. The video recorder can be used to display the image data in a time-lapsed mode, such as in slow motion or frame-by-frame mode to facilitate the viewing of the defect-generated phase change.

In another example embodiment, the power supply 320 is further adapted to modulate the amount of heat generated in the die. For example, increasing the clock frequency causes the die to speed up and generate more heat. The power supply responds to the increased frequency and alters the amount of heat generated in the die, and the frequency can be chosen to correspond to the intrinsic heat source in the die.

In another instance, the system further includes a cooling arrangement 350. The cooling arrangement is adapted to cool the die and to control the advancement of the phase change of the liquid crystal layer. For example, the cooling arrangement can be used to supply a gas, such as compressed air or nitrogen. A filter (not shown) is adapted to remove particulates from the gas, and may be included in the filter arrangement or be located externally to the cooling arrangement. The cooling arrangement may be used alone or in conjunction with altering the power supply to the die for controlling the advancement of the liquid crystal phase change.

Figure 4:
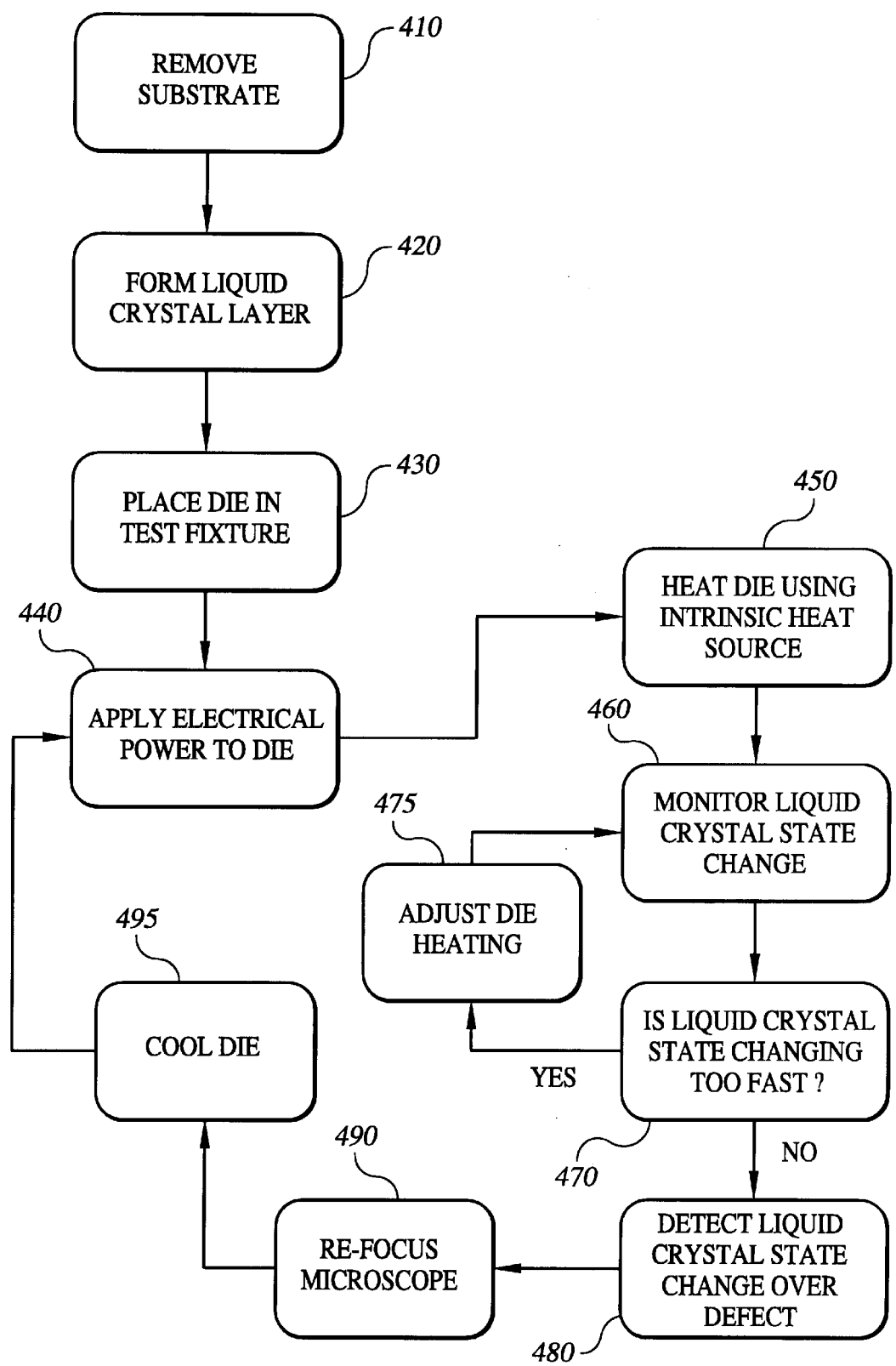
FIG. 4 is a flow diagram of a method for using the system of FIG. 3 for analyzing a semiconductor die, according to an example embodiment of the present invention.

FIG. 4 is a flow diagram of a method for analyzing a semiconductor die using a system, such as the system in FIG. 3, according to another example embodiment of the present invention. Where substrate must first be removed to facilitate sufficient heat transfer to the surface, a substrate removal device is used to remove a portion of substrate from a semiconductor die having an internal heat source at block 410. After the portion of substrate has been removed, a liquid crystal layer is formed on a region exposed by the substrate removal at block 420. For example, adding a solvent such as pentane to liquid crystal and using a deposition arrangement, such as a syringe, to deposit the liquid crystal on the die will form a sufficient liquid crystal layer. A liquid crystal emulsion can also be used and applied using an air blast, such as described hereinabove. Other solvents and/or various types of liquid crystal may also be used.

After the liquid crystal layer is formed, the die is placed in a test fixture at block 430, and powered at block 440. In response to the supplied power, the internal heat source generates heat at block 450. At block 460, the liquid crystal layer is monitored for a state change in response to the generated heat. If the liquid crystal state is changing too fast at block 470, the die heating is adjusted at block 475. The adjustment may include, for example, altering the power supply or using a cooling device to cool the die. Once the adjustment is made, the process continues at block 460.

If the liquid crystal state is not changing too fast at block 470, a liquid crystal state change is detected at block 480. The state change detected is due at least in part to heat generated at a defect in the device, and is detected as a state change that occurs momentarily before the state change being driven by the intrinsic heat source. The detection may include, for example, capturing video images of the state change at an image capture interval sufficiently short to enable the viewing of the defect-generated state change prior to it being engulfed by the intrinsic heat source-driven state change.

In another alternate example embodiment using a microscope to monitor the liquid crystal state change, the microscope is re-focused at block 490 after the state change is detected at block 480. After the microscope is refocused, the die is allowed to cool sufficiently at block 495 so that the liquid crystal changes back to its original state prior to being heated, and the process continues at block 440. In this manner, the location of the defect can be generally detected, and then subsequently more specifically located using the refocused microscope.

In another example embodiment of the present invention, after the defect-related phase change has been detected at block 480 of FIG. 4, the microscope is focused on the defect so that the position of the defect in a viewed image through the microscope is easily determined, such as using time-lapsed analysis. The die being analyzed is then removed from the test fixture. While maintaining the microscope in the same position and focus, another die having similar structure to the die being analyzed and having a portion of the circuitry exposed is placed in the test fixture. The exposed circuitry can then be viewed and, using the known position of the defect in the viewed image, the portion of circuitry having a defect is determined.

In still another example embodiment, discovered in connection with the present invention, a laser-scanning microscope (LSM) can be used to peer through the liquid crystal layer and image the circuitry. By forming the liquid crystal layer at a distance of about 80 microns or less over the circuitry, the image of the defective circuitry can be obtained with the die being analyzed. In addition, by forming the liquid crystal layer at a distance of about 5–10 microns over the circuitry, other commonly-available microscopes can be used to image the circuitry. Imaging through the liquid crystal in this manner can be readily accomplished using a time-lapsed analysis such as described hereinabove. Accordingly, using this example embodiment in connection with FIG. 4, after the liquid crystal state change has been detected at block 480, the circuitry below the defect-related state change can be detected.

While the present invention has been described with reference to several particular example embodiments, those skilled in the art will recognize that many changes may be made thereto without departing from the spirit and scope of the present invention, which is set forth in the following claims.

What is claimed is:

1. A method for analyzing a semiconductor die having a liquid crystal layer, the method comprising:
   generating sufficient heat in the die to cause a first circuit region and a second circuit region to each effect a phase change in corresponding areas of the liquid crystal layer; and
   using time-lapsed analysis, detecting the liquid crystal phase change in the area corresponding to the second circuit region before the corresponding areas cease to be separately detectable.

2. The method of claim 1, wherein the first and second circuit regions are located such that a phase change effected by the first circuit region causes the phase change effected by the second circuit region to be undetectable using real-time analysis, and wherein detecting the liquid crystal phase change in the area corresponding to the second circuit region before the corresponding areas cease to be separately viewable includes using a detector adapted to detect the liquid crystal phase change in the area corresponding to the second circuit region before the corresponding areas cease to be separately viewable.

3. The method of claim 2, wherein the detector is adapted to capture an image of the phase change in the area corresponding to the second circuit region, and wherein the image is distinct from the phase change in the area corresponding to the first circuit region.

4. A method for analyzing a semiconductor die having a liquid crystal layer, the method comprising:
   generating sufficient heat in the die to cause a first circuit region and a second circuit region to each effect a phase change in corresponding areas of the liquid crystal layer including electrically operating the first circuit region; and
   using time-lapsed analysis, detecting the liquid crystal phase change in the area corresponding to the second circuit region before the corresponding areas cease to be separately detectable.

5. The method of claim 1, wherein the first and second regions are selected so that the corresponding phase changes cease to be separately viewable by a human eye viewing the image via a microscope.

6. A method for analyzing a semiconductor die having a liquid crystal layer, the method comprising:
   generating sufficient heat in the die to cause a first circuit region and a second circuit region to each effect a phase change in corresponding areas of the liquid crystal layer; and
   using time-lapsed analysis, detecting the liquid crystal phase change in the area corresponding to the second circuit region before the corresponding areas cease to be separately detectable including arranging a microscope having a polarized light source, an analyzer, and a camera to view the semiconductor die.

7. The method of claim 6, wherein the camera is used to record an image of the die as a function of time, the image being indicative of the liquid crystal changing phase.

8. The method of claim 1, wherein detecting the liquid crystal phase change in the area corresponding to the second region includes detecting a defect in the second circuit region.

9. The method of claim 1, further comprising forming the liquid crystal layer over at least a portion of the semiconductor die.

10. The method of claim 9, further comprising thinning a portion of the integrated circuit prior to forming the liquid crystal layer.

11. The method of claim 4, wherein electrically operating the first circuit region includes operating the die in a continuous loop that includes operational conditions that induce a circuit failure.

12. The method of claim 4, wherein electrically operating the first circuit region includes controlling the rate of phase change of the liquid crystal layer corresponding to the first circuit region by adjusting the frequency of the clock.

13. The method of claim 6, further comprising moving the microscope to keep a boundary of the phase change corresponding to the first circuit region within the field of view of the microscope.

14. The method of claim 7, further comprising viewing the recorded image in slow motion.

15. The method of claim 6, further comprising:
   ceasing to generate heat in the die and allowing the liquid crystal to sufficiently cool to transition back into its original phase;
   increasing the magnification of the microscope and focusing on an area of interest; and
   repeating the steps of generating sufficient heat in the die and detecting the liquid crystal phase change.

16. The method of claim 1, further comprising cooling the die and slowing down the rate of phase change.

17. A method for analyzing a semiconductor die having a liquid crystal layer, the method comprising:

generating sufficient heat in the die to cause a first circuit region and a second circuit region to each effect a phase change in corresponding areas of the liquid crystal layer;

using time-lapsed analysis, detecting the liquid crystal phase change in the area corresponding to the second circuit region before the corresponding areas cease to be separately detectable; and cooling the die and slowing down the rate of phase change including directing a cooling agent at the die, the cooling agent comprising at least one of: compressed air and compressed nitrogen.

18. The method of claim 17, further comprising filtering the cooling agent prior to cooling the die.

19. The method of claim 16, wherein cooling the die includes causing at least a portion of the liquid crystal having undergone a phase change to change back into its original phase.

20. A method for analyzing a semiconductor die having a liquid crystal layer, the method comprising:

generating sufficient heat in the die to cause a first circuit region and a second circuit region to each effect a phase change in corresponding areas of the liquid crystal layer;

using time-lapsed analysis, detecting the liquid crystal phase change in the area corresponding to the second circuit region before the corresponding areas cease to be separately detectable; and cooling the die and slowing down the rate of phase change in conjunction with altering the power supply to the die to control the rate of liquid crystal phase change.

21. A method for analyzing a semiconductor die having a liquid crystal layer, the method comprising:

generating sufficient heat in the die to cause a first circuit region and a second circuit region to each effect a phase change in corresponding areas of the liquid crystal layer;

using time-lapsed analysis, detecting the liquid crystal phase change in the area corresponding to the second circuit region before the corresponding areas cease to be separately detectable; and using a laser-scanning microscope to image the second circuit region through the liquid crystal layer.

22. The method of claim 6, further comprising:

focusing the microscope so that the defect-generated phase change is locatable in an image obtained with the microscope;

replacing the semiconductor die with a structurally similar die having a circuit region exposed; and without adjusting the microscope, detecting the defective circuitry by locating the circuitry corresponding to the location of the defect-generated phase change.

23. The method of claim 1, wherein forming a liquid crystal layer comprises placing liquid crystal emulsion material on a surface of the die and directing an air blast at the emulsion sufficient to cause the emulsion to spread evenly over the surface.

* * * * *

UNITED STATES PATENT AND TRADEMARK OFFICE
CERTIFICATE OF CORRECTION

PATENT NO. : 6,576,195 B1
DATED : June 10, 2003
INVENTOR(S) : Eppes

It is certified that error appears in the above-identified patent and that said Letters Patent is hereby corrected as shown below:

<u>Column 2,</u>
Line 45, "The defect detection can used" should read -- The defect detection can be used --.

Signed and Sealed this

Ninth Day of September, 2003

JAMES E. ROGAN
*Director of the United States Patent and Trademark Office*